US009249393B2

(12) United States Patent
Gimble et al.

(10) Patent No.: US 9,249,393 B2
(45) Date of Patent: Feb. 2, 2016

(54) ADIPOSE DERIVED ADULT STEM CELLS IN HEPATIC REGENERATION

(75) Inventors: Jeffery M. Gimble, Baton Rouge, LA (US); John W. Ludlow, Carrboro, NC (US)

(73) Assignees: BOARD OF SUPERVISORS OF LOUISIANA STATE UNIVERSITY AND AGRICULTURAL AND MECHANICAL COLLEGE, Baton Rouge, LA (US); ARTECEL, INC, Sunnyvale, CA (US)

( * ) Notice: Subject to any disclaimer, the term of this patent is extended or adjusted under 35 U.S.C. 154(b) by 563 days.

(21) Appl. No.: 11/738,887

(22) Filed: Apr. 23, 2007

(65) Prior Publication Data
US 2007/0249045 A1    Oct. 25, 2007

Related U.S. Application Data

(60) Provisional application No. 60/794,508, filed on Apr. 25, 2006, provisional application No. 60/894,128, filed on Mar. 9, 2007.

(51) Int. Cl.
C12N 5/00    (2006.01)
C12N 5/071   (2010.01)

(52) U.S. Cl.
CPC ............. *C12N 5/0672* (2013.01); *C12N 5/067* (2013.01); *C12N 2500/30* (2013.01); *C12N 2500/38* (2013.01); *C12N 2500/42* (2013.01); *C12N 2500/62* (2013.01); *C12N 2500/90* (2013.01); *C12N 2501/11* (2013.01); *C12N 2501/115* (2013.01); *C12N 2501/12* (2013.01); *C12N 2501/23* (2013.01); *C12N 2501/237* (2013.01); *C12N 2506/1384* (2013.01)

(58) Field of Classification Search
CPC ....... A61K 35/28; A61K 35/35; A61K 38/39; C12N 5/0667
See application file for complete search history.

(56) References Cited

U.S. PATENT DOCUMENTS

| | | | |
|---|---|---|---|
| 5,426,098 A * | 6/1995 | Carlino | 514/12 |
| 5,750,376 A * | 5/1998 | Weiss et al. | 435/69.52 |
| 6,153,432 A | 11/2000 | Halvorsen et al. | |
| 6,391,297 B1 | 5/2002 | Halvorsen | |
| 6,429,013 B1 | 8/2002 | Halvorsen et al. | |
| 6,555,374 B1 | 4/2003 | Gimble et al. | |
| 6,841,150 B2 | 1/2005 | Halvorsen et al. | |
| 7,001,746 B1 | 2/2006 | Halvorsen et al. | |
| 7,033,587 B2 | 4/2006 | Halvorsen et al. | |
| 7,332,336 B2 | 2/2008 | Ochiya et al. | |
| 7,413,897 B2 | 8/2008 | Reid et al. | |
| 2005/0042748 A1 * | 2/2005 | Ochiya et al. | 435/366 |

FOREIGN PATENT DOCUMENTS

| | | |
|---|---|---|
| JP | 2005-095138 A | 4/2005 |
| WO | WO 01/62901 | 8/2001 |

OTHER PUBLICATIONS

Kumar D et al. 2005. Transforming growth factor-beta 2 enhances differentiation of cardiac myocytes from embryonic stem cells. Biochem Biophys Res Comm 332: 135-141.*
Liao R. 2005. Yin and yang of myocardial transforming growth factor beta 1: timing is everything. Circulation 111: 2416-2417.*
"Primary." in Merriam-Webster's Online Medical Dictionary hosted by the National Library of Medicine. Accessed online at <http://www.merriam-webster.com/medlineplus/primary> on Apr. 26, 2010. 1 page.*
Barrilleaux B et al. 2006. Review: Ex vivo engineering of living tissues with adult stem cells. Tiss Eng 12: 3007-3019.*
O'Connor KC et al. 2003. Extracellular matrix substrata alter adipocyte yield and lipogenesis in primary cultures of stromal-vascular cells from human adipose. Biotechnol Lett 25: 1967-1972.*
Sgodda M et al. 2007. Hepatocyte differentiation of mesenchymal stem cells from rat peritoneal adipose tissue in vitro and in vivo. Exp Cell Res 313: 2875-2886.*
Schmelzer E., et al., Human Hepatic Stem Cells from Fetal and Postnatal Donors, *Journal of Experimental Medicine* 204(8): 1973-1987, 2007 (the "JEM article").
English Translation of Search Report of TW Patent Application No. 96114414, dated Aug. 17, 2012, 1 page.
Nakagami et al., "Novel Autologous Cell Therapy in Ischemic Limb Disease Through Growth Factor Secretion by Cultured Adipose Tissue—Derived Stromal Cells," Arterioscler. Thromb. Vasc. Biol., 2005, vol. 25, pp. 2542-2547.
Reasons for Rejection in Japanese Patent Application No. 2009-507919, dated Jul. 3, 2012, 3 pages. (English translation).
European Supplementary Search Report in EP 07 76 1121, dated Oct. 13, 2009.
Guilak et al., "Clonal analysis of the differentiation potential of human adipose-derived adult stem cells," *Journal of Cellular Physiology*, vol. 206, No. 1, Jan. 1, 2006, pp. 229-237.
International Search Report in PCT/US2007/67216, dated Oct. 8, 2008.
Invitrogen by Life Technologies, "Introduction to Cell Culture," GIBCO® Cell Culture Basics, 2 pages, last viewed on Oct. 26, 2010 at http://www.invitrogen.com/site/us/en/home/References/gibco-cell-culture-basics/introduc . . . .
Petersen et al "Bone marrow as a potential source of hepatic oval cells" *Science*, vol. 284, May 14, 1999, pp. 1168-1170.
Seluanov et al., "Establishing primary adult fibroblast cultures from rodents," Pub Med, last viewed on Oct. 26, 2010 at http://www.ncbi.nlm.nih.gov/pubmed/20972406.

(Continued)

*Primary Examiner* — Lora E Barnhart Driscoll
(74) *Attorney, Agent, or Firm* — Gilberto M. Villacorta; Natasha Iyer; Foley & Lardner LLP

(57) ABSTRACT

The present invention provides a method to derive hepatic stem cells from stem cells derived from non-liver tissue. In one embodiment of the invention, hepatic stem cells are derived from adipose stem cells. The invention also provides a method of enhancing hepatic cytokine production (e.g., HGF) from ASCs, which may be useful in the regeneration of liver tissue when transplanted in vivo. Tissue culture conditions, including media conditions, are provided.

9 Claims, 6 Drawing Sheets

(56) References Cited

OTHER PUBLICATIONS

Seo et al., "Differentiation of human adipose stromal cells into hepatic lineage in vitro and in vivo," *Biochemical and Biophysical Research Communications*, vol. 328, No. 1, Mar. 4, 2005, pp. 258-264 (XP004723767).

Talens-Visconti et al., "Hepatogenic differentiation of human mesenchymal stem cells from adipose tissue in comparison with bone marrow mesenchymal stem cells," *World Journal Gastroenterology*, vol. 12, No. 36, Sep. 28, 2006, pp. 5834-5845.

Talens-Visconti et al., "Human mesenchymal stem cells from adipose tissue: Differentiation into hepatic lineage," *Toxicology in Vitro*, vol. 21, No. 2, 2007, pp. 324-329.

Zuk et al., "Multilineage cells from human adipose tissue: Implications for cell-based therapies," *Tissue Engineering*, vol. 7, No. 2, Apr. 1, 2001, pp. 211-228 (XP002198710).

* cited by examiner

ADIPOSE DERIVED ADULT STEM CELLS IN HEPATIC REGENERATION

CROSS-REFERENCE TO RELATED APPLICATIONS

This application claims priority to U.S. Provisional Application No. 60/794,508, filed Apr. 25, 2006 and U.S. Provisional Application No. 60/894,128, filed Mar. 9, 2007, the disclosures of which are incorporated herein by reference in their entirety.

BACKGROUND OF THE INVENTION

The present invention relates generally to the field of cell based therapies. More specifically, the present invention relates to the derivation of hepatic stem cells from stem cells derived from non-liver tissue.

Liver failure secondary to hepatitis, hepatotoxin exposure, and cirrhosis threatens the lives of thousands in the United States alone. Estimates of yearly direct healthcare costs for liver disease in the U.S. range from $60 billion to over $100 billion. An additional $20-40 billion in disability is paid annually to these patients and their families by the Social Security Administration. Unfortunately, at this time, liver transplantation is the only therapeutic option available to patients other than palliative measures.

However, because of the shortage of donor organs, less than a third of all patients on waiting lists for livers will actually receive one. According to the United Network of Organ Sharing (UNOS), 15,700 patients await liver transplantation in the United States currently, but only 4,000 to 5,000 transplantable donor livers are available annually. Since, with few exceptions, one donor organ helps only one recipient, over the past decade an increasing gap has grown between available donors and waiting transplant candidates. Therefore, novel therapies are needed.

Stem cell therapies present an alternative therapeutic option for those requiring whole or partial reconstitution of liver function. In many ways, liver cell therapies are a desirable alternative to whole organ transplantation, because one liver can be used to treat multiple patients and because the surgical procedures involved in cell therapies are safer, easier, and less costly for the patient. Stem cell transplantation offers a treatment modality that safely and effectively improves biochemical function within the failing liver.

Thus, there is a need for methods to derive hepatic stem cells from non-liver tissue.

SUMMARY OF THE INVENTION

In one embodiment of the present invention, a method of deriving hepatic stem cells from non-liver stem cells is provided comprising: (a) providing stem cells derived from non-liver tissue; and (b) culturing the stem cells on an extracellular matrix comprising at least one fibrillar matrix protein and in serum-free culture medium comprising hepatocyte growth factor (HGF), in which the stem cells derived from non-liver tissue differentiate into hepatic stem cells. Examples of non-liver tissue, included, but are not limited to spleen, gut, and adipose tissue. In a preferred embodiment, adipose stem cells are derived from adipose tissue the source of non-liver stem cells; however, the non-liver tissue may be from any adult mammal. The at least one fibrillar matrix protein is preferably selected from the group consisting of collagen I and collagen III. In some embodiments of the invention, the culture medium may further comprise Oncostatin M, DMSO or both and the extracellular matrix may further comprise fibronectin, MATRIGEL (i.e., a basement membrane matrix secreted by mouse tumor cells), PORCOGEN or combinations thereof.

In some embodiments, greater than about 70% of the stem cells derived from non-liver tissue differentiate into hepatic stem cells.

In another embodiment of the present invention, a method of inducing HGF expression from non-liver stem cells is provided comprising: (a) providing stem cells derived from non-liver tissue; and (b) culturing the stem cells on an extracellular matrix comprising at least one fibrilar matrix protein and in serum-free culture medium comprising EGF, bFGF, or both, in which the stem cells derived from non-liver tissue produce HGF. The culture medium may further comprise sodium ascorbic diphosphate.

DETAILED DESCRIPTION OF THE EMBODIMENTS

Figure 1:
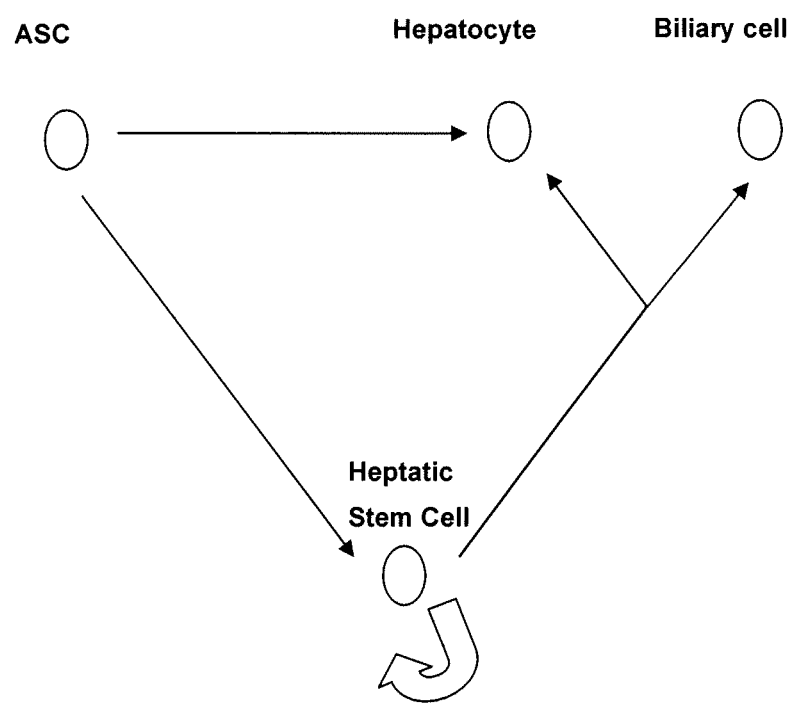
FIG. 1 is schematic depiction of the derivation of hepatic stem cells from non-liver stem cells (e.g., ASCs) according to the instant invention.

The instant invention is directed to methods for the derivation of hepatic stem cells from non-liver tissue. The invention is not limited to tissue from any one stage of life. That is, methods of the present invention may comprise adult, fetal or embryonic tissues. What is more, the source of tissue is broadly directed to any non-liver tissue. Non-limiting examples of "non-liver" tissue include adipose tissue, gut, brain, umbilical cord blood and bone marrow. Thus, while much of the invention will be described herein with reference to adult adipose tissue, such reference is merely exemplary and should not be construed as limiting.

Derivation of Non-Liver Stem Cells from Non-Liver Tissue

Non-liver stem cells may be derived from adipose tissue (i.e., adipose stem cells, "ASCs"), either from human or other mammalian sources. Human ASCs may be isolated from subcutaneous adipose tissue obtained from preferably healthy, male or female patients, e.g., those undergoing elective liposuction procedures. Murine ASCs may also be isolated from subcutaneous adipose tissue obtained from, preferably, male C57BL/6 mice and/or from male ROSA-26 mice. From these sources, within 5 days of culture, recovery of about 250,000 ASCs from one milliliter of liposuction aspirate is typical. The average human liposuction specimen is greater than about 500 ml. Even greater numbers of cells are recovered from equal volumes of murine adipose tissue, presumably due to the young age of the donor animals.

Methods of deriving adipose stem cells from adipose tissue are presented in U.S. Pat. Nos. 6,153,432, 6,391,297, 6,429,013, 6,555,374, 6,841,150, 7,001,746 and 7,033,587, the disclosures of which are incorporated herein in their entirety by reference. Briefly, in one example, once the tissue is procured, it is subjected to differential centrifugation and expanded in culture. A single gram of tissue typically yields between 50,000 to 100,000 stem cells within 24 hours of culture. Expansion media preferably comprises 60% DMEM (low glucose) and 40% MCDB-201 supplemented with 10% fetal bovine serum (FBS); 5 µg/ml insulin, 5 µg/ml transferrin and 5 ng/ml selenium; $10^{-9}$M dexamethasone; 10 ng/ml epidermal growth factor (EGF) and/or 10 ng/ml fibroblast growth factor, basic (bFGF); $10^{-4}$ M ascorbic acid 2-phosphate; 100 U/ml penicillin; and 100 U/ml streptomycin. Without being held to or bound by theory, it is believed that the addition of EGF, bFGF, or both, to the media enhances the ability of the ASCs to later differentiate into hepatic stem cells. Ascorbic acid 2-phosphate may have a similar effect upon ASCs particularly with respect to their ability to express HGF (discussed below).

HGF promotes differentiation of stem cells toward the hepatic lineage. The addition of HGF to the present culture conditions, where indicated, is thought to be able to complement the process of differentiation. Hence, in one embodiment of the present invention, the production of HGF from the cell populations described herein may be used in vitro and in vivo (e.g., upon transplantation) to aid in the differentiation of otherwise "nascent" stem cells into functional hepatocytes.

Differentiation Media

In the presence of dexamethasone, insulin, isobutylmethylxanthine and a thiazolidinedione, ASCs undergo adipogenesis. The cells accumulate lipid vacuoles, which can be stained for neutral lipid and express adipocyte-specific markers, including the secreted cytokine leptin and the fatty acid binding protein aP2. However, the differentiation potential of the ASCs is not limited to the adipocyte lineage. For differentiation to hepatic stem cells and hepatocytes, the serum-free expansion medium is further supplemented with 10 ng/ml EGF and/or 10 ng/ml bFGF, 10 ng/ml HGF, 10 ng/ml Oncostatin M (OSM), 1% DMSO, or combinations thereof.

Differentiation Conditions

ASCs are initially plated with expansion media at a density of about $5-15\times10^3$ cells/cm$^2$ on a tissue dish or well pre-coated with collagen I. Collagen-I coated tissue dishes are commercially available (e.g., PORCOGEN), any of which may be used with the instant invention. In addition, without being held to or bound by theory, the present inventors have learned that the use of fibrilar liver matrix proteins (e.g., collagens, preferably collagens I and collagen III) are preferred in the inventive method as their use appears to better reproduce the in vivo environment of stems cells found in adult hepatic tissue. In other words, the fibrilar matrix proteins appear to provide differentiation signals that are either not available or not as strong with other matrix proteins.

Fibronectin, for example, is a non-fibrilar molecule; it is a glycoprotein (collagens are not glycoproteins), which primarily allows cells to attach to the other matrix molecules or the tissue culture dish. That is, fibronectin is thought to be a bridge to link integrins on the cell surface to the underlying collagen matrix in the organ (in vivo) or the bottom of a tissue culture dish (in vitro). Thus, the signals that are activated by fibronectin binding are likely quite different than those activated by collagen binding. While the use of non-fibrilar proteins, such as fibronectin are not required, they may be used in conjunction with fibrilar proteins according to the invention. In some embodiments, the extracellular matrix comprises no fibronectin.

In this way, it is believed that the present method directs the "conversion" of non-liver stem cells to hepatic stem cells, which in some cases may then differentiate into mature hepatocytes, rather than a direct differentiation of non-liver stem cells directly into hepatocytes, bypassing the hepatic stem cell stage all together. This notion is depicted schematically in FIG. 1. Examples of other matrix proteins, which may be suitable in the present invention, include embryonic liver matrix proteins.

During this initial period, the cells are allowed to reach greater than about 80% confluence, which may take up to 3 days, and incubated in the expansion media described above. Upon reaching greater than about 80% confluence, the cells are washed two or three times with phosphate buffered saline (PBS) alone and subsequently placed in serum-free differentiation media. The ASCs are maintained under these culture conditions for an additional period of 4 to 20 days for differentiation to take place. Representative cultures may be harvested at regular intervals for analysis.

EXAMPLE 1

Human ASCs were plated in (serum-free) expansion medium. After 2-3 passages, the cell population was dispersed with trypsin and seeded at a density of 5,000 to 10,000 cells per cm$^2$ on collagen I-coated dishes. The cells were propagated until about 80% confluence was attained, at which time the media was changed to hepatic differentiation medium [comprised of serum-free expansion media supplemented with 10 ng/ml HGF, 10 ng/ml Oncostatin M (OSM), and 0.1% DMSO]. The medium was changed every three days.

Cell lysates were collected at various time points post-differentiation for RT-PCR analysis or fixed for histological analysis of hepatic biomarkers. Some of the biomarkers used to assess in vitro hepatogenesis included: (a) albumin (ALB) and α-fetoprotein (AFP) expression by RT-PCR; and (b) glycogen storage (a later stage hepatic marker assayed by positive PAS staining).

Figure 2:
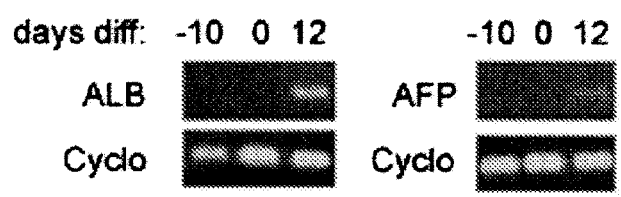
FIG. 2 shows relative albumin (ALB) and alpha-fetoprotein (AFP) mRNA expression in hepatic stem cells derived from ASCs.

FIG. 2 shows AFP and ALB expression of ASCs incubated for 10 days in differentiation media. Total RNA was purified from cells using commercially available kits. 2 µg of total RNA was reverse transcribed using MMLV-RT with Oligo dT at 42° C. for 1 hour in a 20 µl reaction. 40 cycles of PCR were performed using 2 µl diluted (1:10) cDNA. 5 µl of the amplified products were separated on a 2% agarose gel and visualized with EtBr. (Cyclophilin B (Cyclo) was used as control for input cDNA.) The data show that while albumin is expressed in the population, little to no AFP is present in same population, which is indicative of a population of cells substantially comprising hepatic stem cells. Indeed, it is believed that AFP expression indicates the presence of more mature hepatic cells which may have differentiated from the hepatic stem cells. Further analysis confirmed that these cells exhibited other markers of hepatic stem cells, including positive expression of Ep-CAM and ICAM-1 and negative expression of MHC class Ia.

Figure 3:
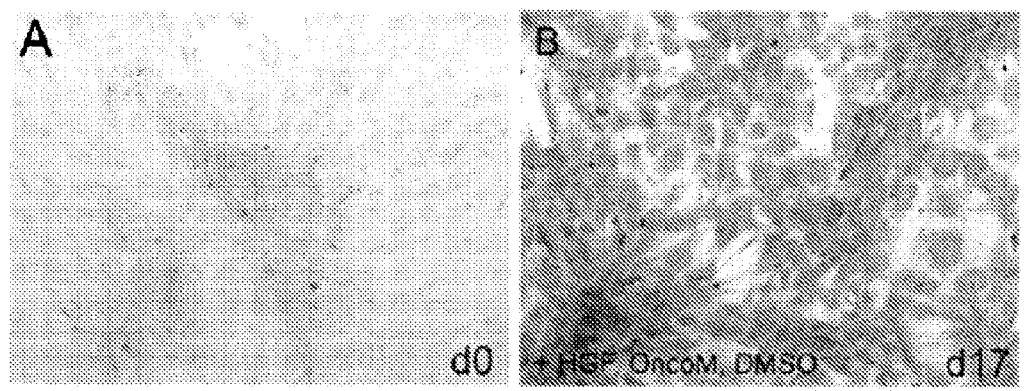
FIG. 3 shows glycogen storage in hepatic stem cells derived from ASCs.
Figure 4:
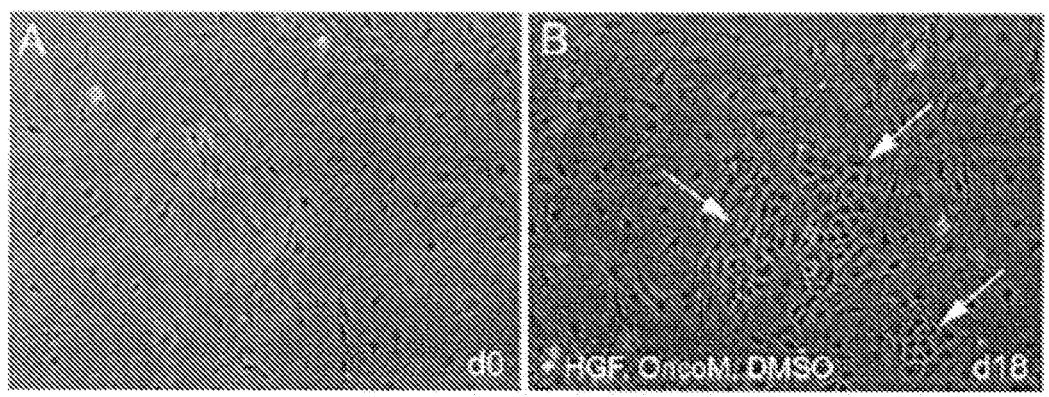
FIG. 4 shows the morphology of hepatic stem cells derived from ASCs.

FIG. 3 shows early passage [p3] ASCs seeded onto 6-well dishes, grown to about 80% confluence and switched to hepatic differentiation medium. Individual wells were fixed at day 0 (panel A) and day 17 (panel B), and stained for glycogen (dark shading). FIG. 4 further shows cells, which have been incubated for 18 days in differentiation conditions, have hepatocyte morphology.

Taken together, these data indicate that ASCs can be differentiated into hepatic stem cells. Some of these stem cells then may mature into hepatocytes or biliary cells, (FIG. 1) but may also self regenerate.

In another embodiment of the invention, a method is provided for inducing the expression of cytokines that may play a role in liver regeneration from ASCs. Such cytokines may include HGF, VEGF, IL-6, LIF, TNFα, leptin and combinations thereof. The present invention provides culture conditions for enhancing the production of one or all of these cytokines. Again, without being held to or limited by theory, the present inventors have learned that the used of fibrilar matrix proteins (e.g., collagen I), generally, are preferred in the inventive method as their use appears to better reproduce the in vivo environment of hepatic stem cells in adult tissue. What is more, incorporation of EGF alone or with sodium ascorbate appears to substantially enhance the production of cytokines under these conditions. Additional factors/conditions that can contribute to production of hepatic regenerative cytokines include, phorbol esters, FGFs, heparin, hypoxia (defined as <5% $O_2$) or combinations thereof.

EXAMPLE 2

Figure 5:
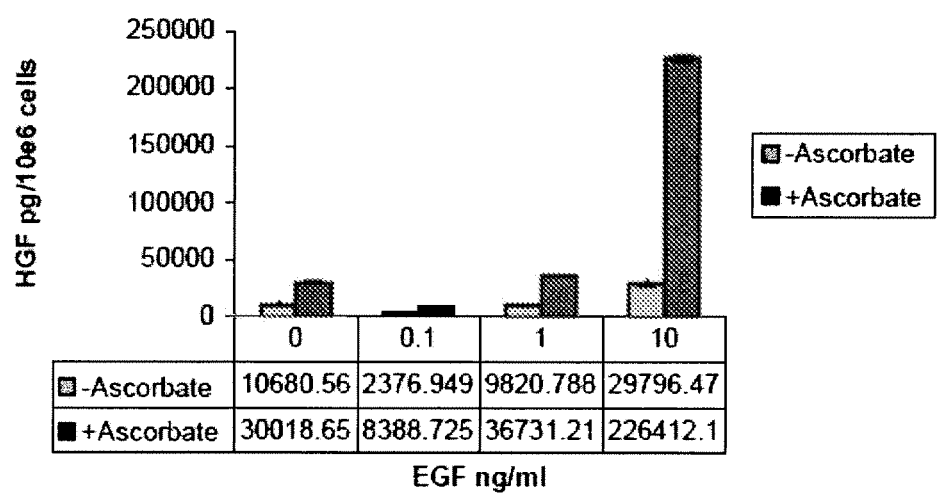
FIG. 5 provides a graph showing that EGF and sodium ascorbic diphosphate have the concerted ability to induce HGF expression in human ASCs.

Human ASCs were propagated in DMEM/F12 media supplemented with 3% serum and the effect of EGF and sodium ascorbate diphosphate on cytokine production was determined. Triplicate wells, seeded at $5-10 \times 10^3$ cells per $cm^2$ were incubated with EGF at concentrations of 0, 0.1, 1 or 10 ng/ml+/−sodium ascorbate diphosphate. After 72 hours, the media was collected for ELISA detection of HGF. FIG. 5 is representative of the data, normalized to pg HGF/$10^6$ cells (n=3). Media alone did not contain HGF. The data demonstrates that in the absence of EGF and sodium ascorbate, HGF is synthesized at over 10,680 pg/$10^6$ cells. However, this production is increased nearly 5-fold in the presence of both factors.

EXAMPLE 3

Figure 6:
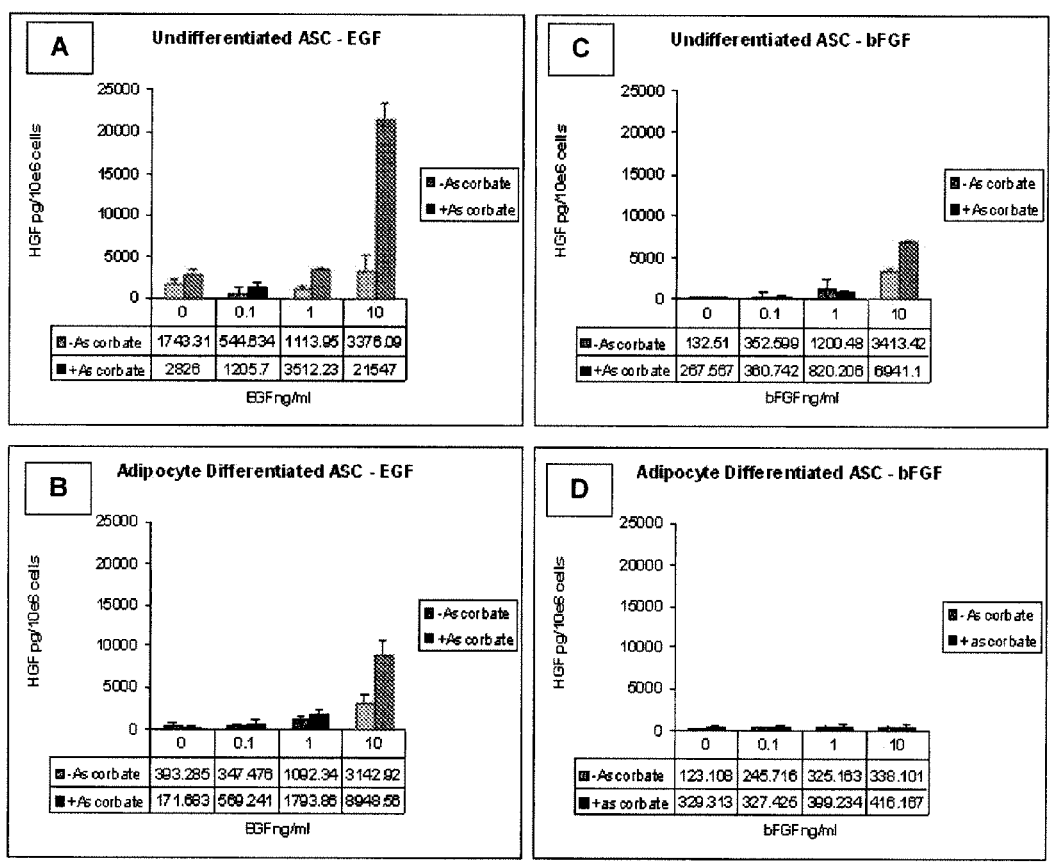
FIG. 6 provides a graph comparing the ability of EGF and bFGF with or without ascorbic diphosphate to induce HGF expression in ASCs.

Undifferentiated human ASCs were propagated in DMEM/F12 media supplemented with 3% serum and 10 ng/ml or either EGF or bFGF. FIG. 6A shows that in the presence of EGF, undifferentiated ASCs expressed HGF in levels greater than 3000 ng/million cells, which reflects a 2-fold increase relative to baseline levels. The presence of ascorbic acid 2-phosphate further increased the inductive effect of EGF to a 25-fold induction. Under the same conditions, adipocyte differentiated ASCs expressed HGF levels an additional 2.0- and 6.3-fold, in the absence or presence of ascorbic acid 2-phosphate, respectively. (FIG. 6B) In the presence of bFGF, expression of HGF by undifferentiated huASCs was also statistically increased. (FIG. 6C) However, bFGF failed to affect HGF expression from adipocyte differentiated ASCs. (FIG. 6D).

Figure 7:
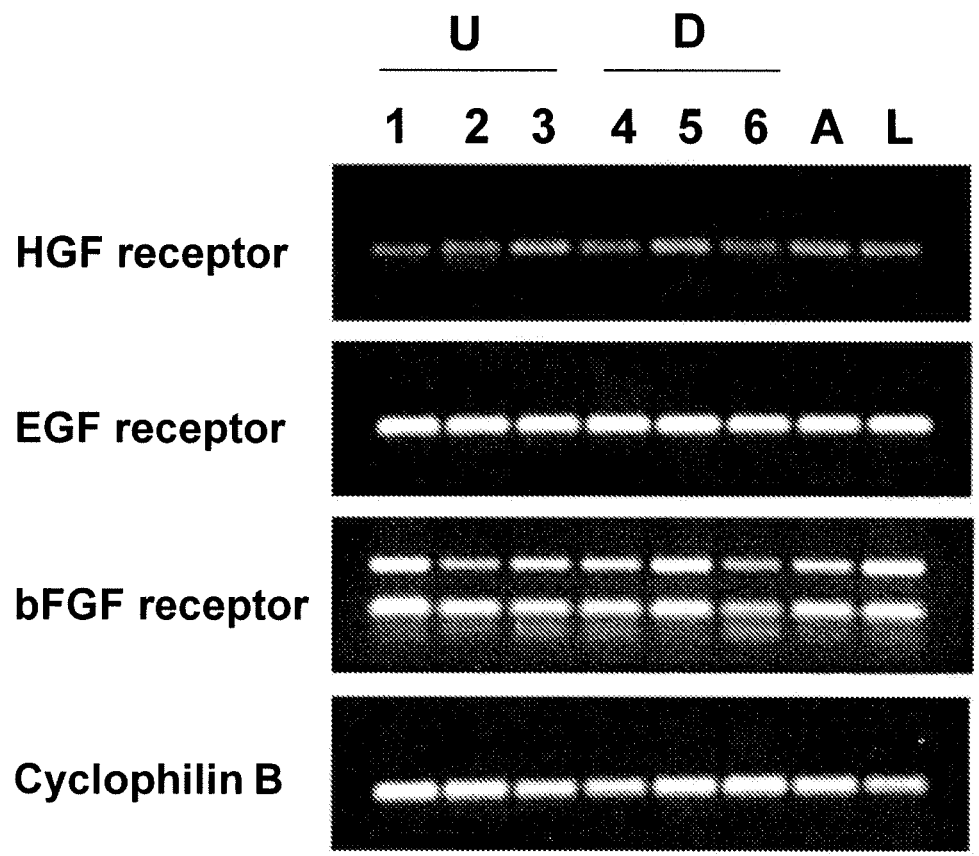
FIG. 7 is an RT-PCR analysis of receptors expressed in ASCs.

Subsequent analysis of total RNA by RT-PCR demonstrated that both undifferentiated and adipoctye differentiated huASCs expressed the bFGF and EGF receptor, as well as that of HGF (c-met) receptor (FIG. 7).

ASC Cytokine Expression

Figure 8:
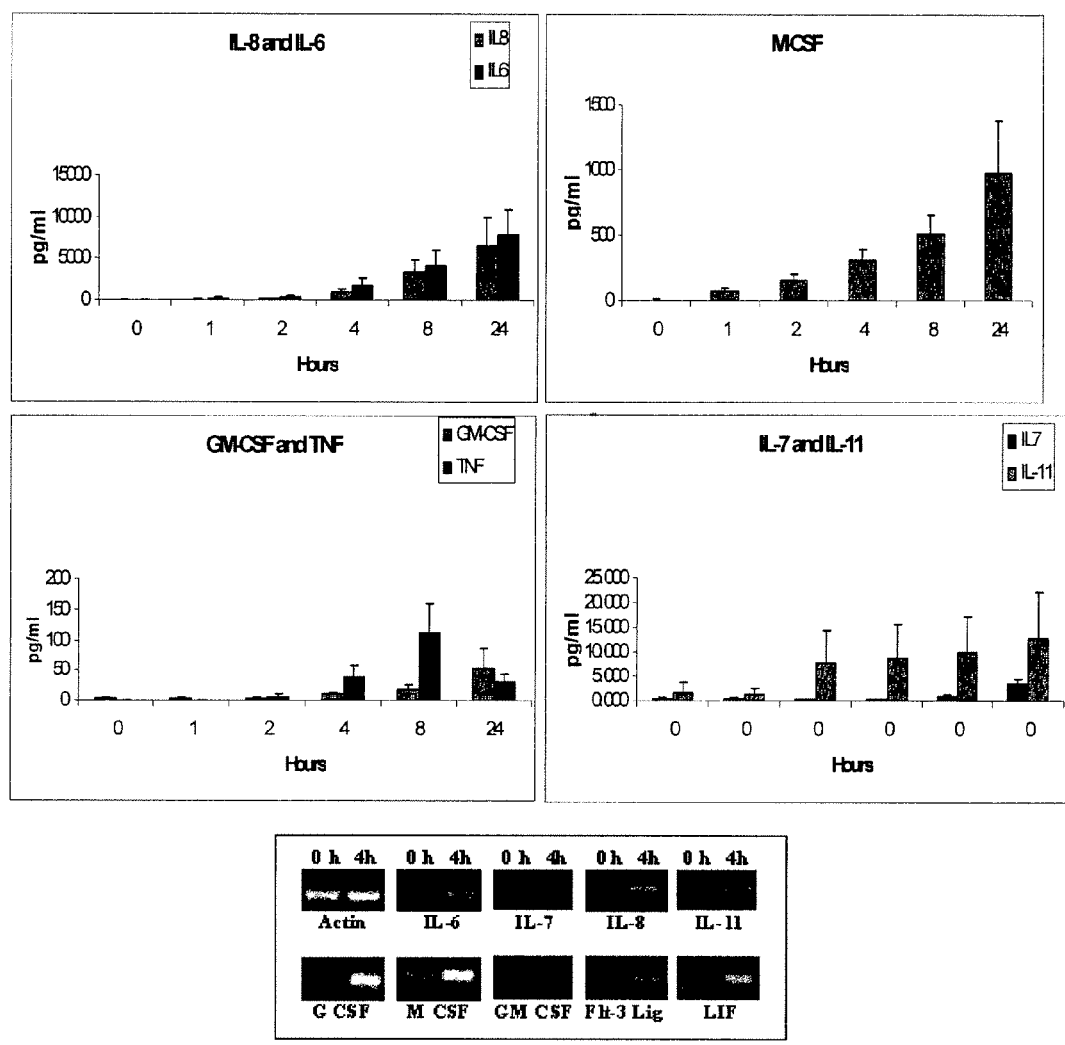
FIG. 8 shows the secretion of selected cytokines (n=6 to 8 ASC donors) at varying times following exposure to lipopolysaccharide for periods of 0 to 24 hours.

In addition to HGF, human ASCs secrete a wide range of hematopoietic and other functional cytokines. When induced with lipopolysaccharide (LPS, 100 ng/ml), otherwise quiescent ASC cultures exhibit an increased steady state level of the mRNAs for the interleukins 6, 7, 8, and 11 (IL-6, -7, -8, -11); leukemia inhibitory factor (LIF); macrophage-colony stimulating factor (M-CSF); granulocyte-macrophage-colony stimulating factor (GM-CSF); granulocyte-colony stimulating factor (G-CSF); flt-3 ligand (Flt3L) as shown in FIG. 8 as well as kit ligand (KL, also known as stem cell factor); tumor necrosis factor α (TNFα); and the bone morphogenetic proteins 2 and 4 (BMP-2, -4). Both murine and human bone marrow-derived stem cells also express these same cytokines. As shown in Table 1 below and FIG. 8, the ASCs significantly increase their secretion of IL-6, IL-7, IL-8, GM-CSF, and M-CSF within 24 hours after LPS stimulation.

TABLE 1

LPS induction of secreted cytokines (ELISA, pg/ml)

| | Time LPS | | |
|---|---|---|---|
| | 0 hour | 8 hours | 24 hours |
| M-CSF | 4 ± 3 | 512 ± 98 | 977 ± 285 |
| TNFα | 0 ± 0 | 112 ± 82 | 30 ± 22 |
| IL-1 α/β | N.D. | N.D. | N.D. |
| IL-6 | 1 ± 1 | 6083 ± 956 | 9204 ± 2676 |
| IL-7 | 0.4 ± 0.2 | 0.9 ± 0.2 | 3.4 ± 0.7 |

In this way, ASCs transplanted immediately or soon following a hepatic injury can enhance liver regeneration, in part, through the local release of HGF and VEGF. Introduction of ASCs into a mammal may be accomplished by any of the methods known and available in the art, including injection. In another method of cell delivery, ASCs are transplanted into the recipient mammal via intraparenchymal or intrahepatic injection after encapsulation. Transplanting cells embedded in, for example, an alginate matrix, offers several advantages, including: (a) providing cells a "3-D environment" that improves viability after implantation; (b) allowing a higher number of cells to be implanted; (c) creating a microenvironment supportive for growth and differentiation; and (d) allowing co-encapsulation of factors (e.g., growth factors or multiple cell types as described above) prior to transplantation.

In addition, since the cells are embedded in a hydrogel, they are less prone to disperse to other sites of the body as is frequently observed when cell suspensions are used for transplantations.

Briefly, cell encapsulation is performed using an electrostatic bead generation apparatus after mixing cells in a solution of sodium alginate. The beads are resuspended in PBS at a cell concentration equivalent to about $10^7$ cells/ml. A minilaparotomy incision is performed using sterile technique after achieving adequate anesthesia and sedation of the donee. The cell suspension is delivered by direct injection via needle into the periphery of the tissue (delivery of 0.1 ml is usual in mice) with hemostasis achieved through topical compression. This technique may be equally applicable to humans and murine models.

In a second transplantation methodology, up to $10^6$ cells may be injected intrasplenically after attachment to Cytodex 3™ Pharmacia) microcarrier beads. After transplantation, cells rapidly translocate to the liver sinusoids and can be detected in the liver within two hours of transplantation.

Dosing

For humans, a "dose" of about $3 \times 10^9$ cells or 1% of liver mass when injected directly into the hepatic circulatory system is preferred based on experience with this dose in mouse studies. Indeed, in mice a dose of 2 million cells is preferred. The mid and high dose levels of 4 and 6 million cells, respectively, were based on results of a pilot acute lethality study in which groups of 3 male NOD-SCID mice each were administered doses of 0, 2.5, 5, 10, 20 and 40 million human liver cells in one milliliter volume. Transplantation of 10, 20 and 40 million cells resulted in 100% mortality and transplantation of 5 million cells produced mortality in 1 of 3 mice within 20 hours, whereas 2.5 million cells per mouse were well tolerated. The high dose of 6 million cells, to be administered in a 0.2 ml dose volume, was selected because it was considered to be the maximum dose that can be administered without splenic rupture and the majority of the animals were expected to tolerate the dose (i.e., an MTD). The mid dose of 4 million cells is preferred as a mid-point between the low and high dose levels.

Particularly when treating humans, all processing steps should be conducted according to cGMP standards with appropriate SOPs. The human ASCs are preferably isolated by trypsin digestion. Cells could be used immediately or cryopreserved prior to use. The human ASCs, if cryopreserved, would be thawed and suspended in a serum free, iso-osmotic media suitable for infusion at a concentration of no less than about 0.1 and no more than 10 million cells per ml. Cell viability may be assessed by typhan blue exclusion or equivalent assay. Cells would be stored at room temperature or on wet ice and assessed by microscopic examination for evidence of any clumping. If observed, the cells would be subjected to selection over a nylon mesh (40 micron) filter and the final concentration of cells re-determined. Cells would be infused intravenously into a recipient suffering from liver damage (e.g., due to acute toxin exposure) at a dose of 1 to 10 million cells per kg of body weight. Recipients would be monitored for evidence of any acute reactions, such as fever, chills, or change in mental status, and if these were observed, would be treated symptomatically by standard medical practice. Subjects would then be monitored over the following 2 month period by weekly serum chemistries to assess liver function recovery.

As such, this invention may benefit the treatment of multiple forms of liver failure, both acute and chronic. The availability of either autologous or allogeneic human ASCs as an adult stem cell for improving liver function has value for patients suffering liver damage secondary to a toxin exposure (carbon tetrachloride, acetaminophen), to a infectious agent (hepatitis, cytomegalovirus), or to surgical resection due to tumor metastasis or trauma. The ability of the human ASCs to differentiate into functional hepatocytes and/or to release growth factors supporting the proliferation and differentiation of endogenous hepatocyte progenitors may provide a mechanism to improve and accelerate the recovery of liver function in these conditions.

While the invention has been described in connection with specific embodiments thereof, it will be understood that it is capable of further modifications and this application is intended to cover any variations, uses, or alterations of the invention following. In general, the principles of the invention and including such departures from the present disclosure as come within known or customary practice within the art to which the invention pertains and as may be applied to the essential features hereinbefore set forth and as follows in the scope of the appended claims.

What is claimed is:

1. A method of deriving hepatic progenitor cells from adipose stem cells comprising:
   (a) culturing primary stem cells isolated from adipose tissue on an extracellular matrix comprising collagen I in serum-free culture medium comprising hepatocyte growth factor (HGF), Oncostatin M (OSM), and optionally dimethyl sulfoxide (DMSO), in which the stem cells isolated from adipose tissue differentiate into hepatic stem cells.

2. The method according to claim 1 in which the adipose tissue is tissue from an adult mammal.

3. The method according to claim 1 in which the extracellular matrix further comprises collagen III.

4. The method according to claim 1 in which collagen I is the sole fibrillar matrix protein.

5. The method according to claim 1 in which the culture medium further comprises HGF, Oncostatin M, and DMSO.

6. The method according to claim 1 in which the extracellular matrix further comprises basement membrane matrix secreted by mouse tumor cells.

7. The method according to claim 1 in which greater than about 70% of the stem cells isolated from adipose tissue differentiate into hepatic progenitor cells.

8. The method of claim 1 in which the stem cells isolated from adipose tissue are obtained upon culturing in vitro.

9. The method of claim 1 in which the primary stem cells from adipose tissue are isolated in the presence of sodium ascorbic diphosphate.

* * * * *